US012708153B2

(12) United States Patent
Liu et al.

(10) Patent No.: US 12,708,153 B2
(45) Date of Patent: Aug. 18, 2026

(54) NURSING GARMENT

(71) Applicant: Shenzhen Lute Jiacheng Supply Chain Management Co., Ltd., Shenzhen (CN)

(72) Inventors: Dong Liu, Shenzhen (CN); Lan Li, Shenzhen (CN)

(73) Assignee: Shenzhen Lute Jiacheng Supply Chain Management Co., Ltd., Shenzhen (CN)

( * ) Notice: Subject to any disclaimer, the term of this patent is extended or adjusted under 35 U.S.C. 154(b) by 0 days.

(21) Appl. No.: 19/064,875

(22) Filed: Feb. 27, 2025

(65) Prior Publication Data

US 2026/0206881 A1 Jul. 23, 2026

(30) Foreign Application Priority Data

Jan. 22, 2025 (CN) ........................ 202520158694.5

(51) Int. Cl.
*A41C 3/04* (2006.01)
*A61M 1/06* (2006.01)

(52) U.S. Cl.
CPC ............... *A41C 3/04* (2013.01); *A61M 1/062* (2014.02); *A61M 2209/088* (2013.01)

(58) Field of Classification Search
CPC ........... A41C 3/04; A41C 3/08; A41C 3/0064; A41D 1/21; A41D 1/215
USPC ........................................................... 450/36
See application file for complete search history.

(56) References Cited

U.S. PATENT DOCUMENTS

| | | | | |
|---|---|---|---|---|
| 11,006,678 | B1 * | 5/2021 | Ye | A41C 3/04 |
| 12,161,173 | B2 * | 12/2024 | Zhang | A41C 3/04 |
| 2023/0329359 | A1 * | 10/2023 | Akerson | A41C 3/0014 |

* cited by examiner

*Primary Examiner* — Timothy K Trieu

(57) ABSTRACT

The present application discloses a nursing garment, comprising: a shoulder strap, wherein the shoulder strap has a first connecting structure; an outer layer, wherein the outer layer has a second connecting structure, and the second connecting structure is detachably connectable to the first connecting structure; and an inner layer, wherein the inner layer has a third connecting structure, and the outer layer has a fourth connecting structure, and the third connecting structure is detachably connectable to the fourth connecting structure; wherein the inner layer has an opening, wherein the outer layer is detachably connectable to the shoulder strap via the second connecting structure, such that the outer layer and the inner layer can be detached from the shoulder strap together, thereby at least partially exposing the wearer's breast.

18 Claims, 5 Drawing Sheets

NURSING GARMENT

CROSS-REFERENCE TO RELATED APPLICATIONS

The present application claims priority to Chinese Patent Application No. 202520158694.5, filed on Jan. 22, 2025, the entire contents of which are incorporated herein by reference.

TECHNICAL FIELD

The present application relates to the technical field of maternal and baby products, particularly to a nursing garment.

BACKGROUND

When using a breast pump, the mother must manually position the breast flange or breast shield over the exposed part of the breast. Since using a breast pump to express milk takes a long time, mothers typically express milk from both breasts at the same time. To do so, the mother must hold the breast flanges or shields with both hands, which places them in an awkward position and makes it difficult to perform simple tasks like operating the breast pump. Therefore, breastfeeding women are unable to fully use both hands to complete other tasks. Developing a device that allows the mother to use the breast pump while also having the freedom to use her hands to perform other tasks would be very beneficial.

Hands-free breast pumps enable mothers to simultaneously massage their breasts to encourage milk flow. However, most of the breast pumps currently in use cannot provide this feature, or they do not allow the mother to engage in other tasks while expressing milk. In order to alleviate the drawbacks of holding the breast pump during milk expression, a supportive breast pump or nursing garment typically includes at least two layers. The inner layer has an opening for forming a passage to either breastfeed or insert the breast pump, while the outer layer covers the inner layer to ensure privacy during regular wear.

Traditional nursing garments have problems with difficult disassembly or uncomfortable wearing. When small-sized fasteners are used, interference between several clasps can occur, causing discomfort when the garment is worn, as the clasps may press against the wearer's body. Additionally, the inner and outer layers may not be smoothly disconnected or connected, particularly when fasteners on the shoulder straps and those on the inner or outer layers are connected simultaneously, which can cause the fasteners to pile up and make disassembly difficult, resulting in poor comfort.

SUMMARY

In view of the shortcomings in the existing technology, this application provides a nursing garment that solves the problem of poor disassembly and connection between the layers of the garment.

To solve the above technical problem, an embodiment of the present application adopts the following technical solution: a nursing garment, comprising: a shoulder strap, wherein the shoulder strap has a first connecting structure; an outer layer, wherein the outer layer has a second connecting structure, and the second connecting structure is detachably connectable to the first connecting structure; and an inner layer, wherein the inner layer has a third connecting structure, and the outer layer has a fourth connecting structure, and the third connecting structure is detachably connectable to the fourth connecting structure; wherein the inner layer has an opening, and the opening is configured to support at least a portion of a breast pump inserted into the opening, or the opening is configured to allow a wearer's nipple to be exposed through the opening for breastfeeding; wherein the outer layer is detachably connectable to the shoulder strap via the second connecting structure, such that the outer layer and the inner layer can be detached from the shoulder strap together, thereby at least partially exposing the wearer's breast.

In one embodiment, the shoulder strap has a fifth connecting structure, and the third connecting structure of the inner layer is selectively connectable to either the fourth connecting structure or the fifth connecting structure; after the outer layer and the inner layer are detached from the shoulder strap, the inner layer is connectable to the fifth connecting structure via the third connecting structure to allow the inner layer to support at least a portion of a breast pump inserted into the opening, or to allow the wearer's nipple to be exposed through the opening for breastfeeding.

In one embodiment, wherein one of the first connecting structure and the second connecting structure is a hook structure, and the other is a loop structure, slot structure, or hole structure.

In one embodiment, one of the third connecting structure and the fourth connecting structure is a hook structure, and the other is a loop structure, slot structure, or hole structure.

In one embodiment, one of the first connecting structure and the second connecting structure is a hook side of a hook-and-loop fastener, and the other is the loop side of the hook-and-loop fastener.

In one embodiment, one of the third connecting structure and the fourth connecting structure is a hook side of a hook-and-loop fastener, and the other is the loop side of the hook-and-loop fastener.

In one embodiment, the first connecting structure is a first clasp, the second connecting structure is a second clasp, the first clasp has a first hook, and the second clasp has a slot, wherein the slot is configured to match the first hook.

In one embodiment, the third connecting structure is a second clasp, the fourth connecting structure is a first loop, the second clasp has a second hook, and the second hook is configured to match the first loop.

In one embodiment, the fifth connecting structure is a second loop disposed on the strap.

In one embodiment, the first loop is disposed on the inner surface of the outer layer.

In one embodiment, the opening is formed between three edges of the inner layer, and the three edges at least partially overlap.

In one embodiment, the elasticity of the three edges is greater than the elasticity of other portions of the inner layer.

In one embodiment, any two of the three edges are not parallel to each other.

In one embodiment, the first loop is a sewn loop on the inner surface of the outer layer, the sewn loop is formed by sewing the ends of a fabric strip to the outer layer.

In one embodiment, the first loop is formed by attaching the ends of a fabric strip to the outer layer.

In one embodiment, the second loop is a sewn loop on the shoulder strap, and the sewn loop is formed by sewing the ends of a fabric strip to the shoulder strap.

In one embodiment, wherein the second loop is formed by attaching the ends of a fabric strip to the shoulder strap.

In one embodiment, wherein the inner layer and the outer layer are made of different fabrics.

In one embodiment, wherein the opening is a slit formed on the inner layer.

In one embodiment, wherein the inner layer and the outer layer are made of the same fabric.

The embodiment of the present application provides a nursing garment, comprising: a shoulder strap, wherein the shoulder strap has a first connecting structure; an outer layer, wherein the outer layer has a second connecting structure, and the second connecting structure is detachably connectable to the first connecting structure; and an inner layer, wherein the inner layer has a third connecting structure, and the outer layer has a fourth connecting structure, and the third connecting structure is detachably connectable to the fourth connecting structure; wherein the inner layer has an opening, and the opening is configured to support at least a portion of a breast pump inserted into the opening, or the opening is configured to allow a wearer's nipple to be exposed through the opening for breastfeeding; wherein the outer layer is detachably connectable to the shoulder strap via the second connecting structure, such that the outer layer and the inner layer can be detached from the shoulder strap together, thereby at least partially exposing the wearer's breast, ensuring smooth disassembly and connection between the layers of the nursing garment.

BRIEF DESCRIPTION OF THE DRAWINGS

In order to more clearly illustrate the technical solutions of the embodiments of the present application or prior art, the following provides a brief description of the drawings that are needed in the description of the embodiments or prior art. It is evident that the drawings described below are merely some embodiments of the present application, and that a person skilled in the art, without any inventive effort, can derive other drawings based on the structures shown in these drawings.

Figure 1:
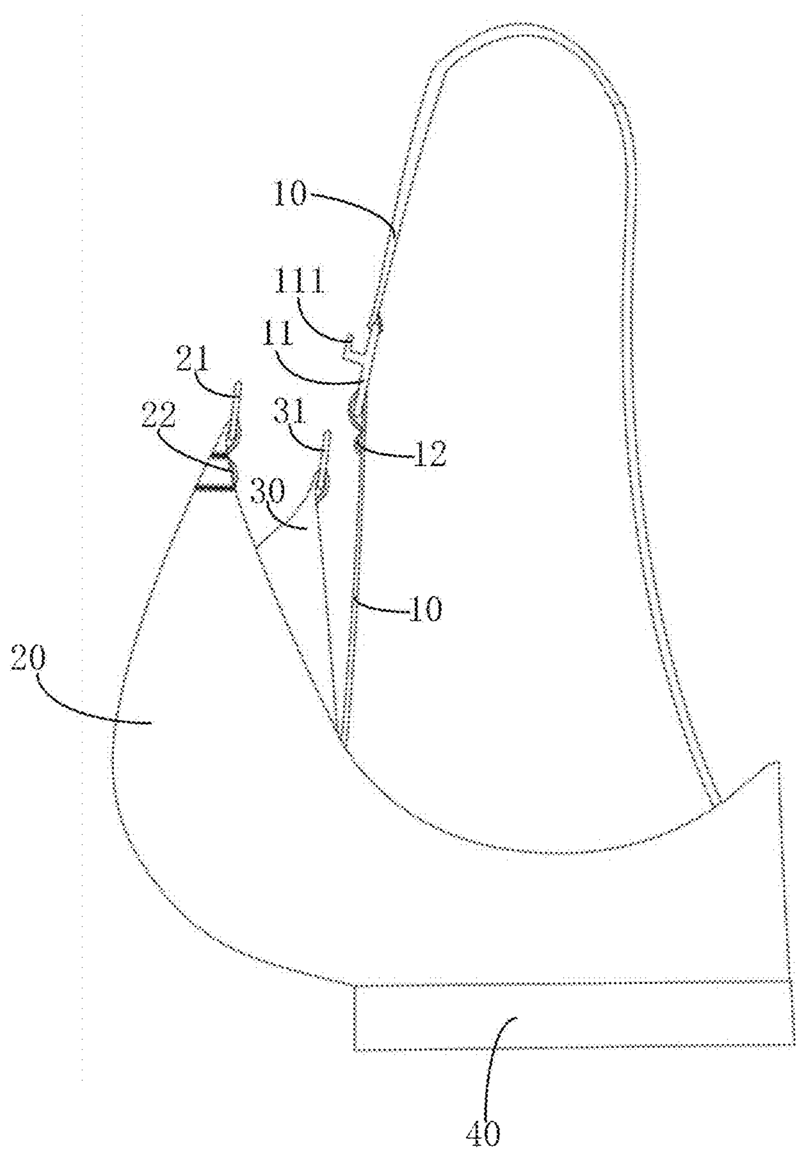
FIG. 1 is a schematic side view of the nursing garment in one embodiment of the present application, showing the state where the inner layer and the outer layer are detached, and the outer layer and shoulder strap are detached.

The implementation, functional features, and advantages of the objectives of this application will be further explained with reference to the embodiments and the accompanying drawings.

DETAILED DESCRIPTION OF THE EMBODIMENTS

In the present application, the terms "dispose", "have", and "connect" should be broadly interpreted. For example, it can refer to fixed connecting, detachable connecting, or integral construction; it can refer to mechanical connecting or electrical connecting; it can refer to direct connecting or indirect connecting through an intermediate medium, or internal communication between two devices, components, or parts. For those skilled in the art, these terms can be understood in specific contexts.

The terms "center", "longitudinal", "lateral", "length", "width", "thickness", "up", "down", "front", "back", "left", "right", "vertical", "horizontal", "top", "bottom", "internal", "external", "radial", "circumferential", etc., indicating orientation or positional relationships are based on the orientation or positional relationships shown in the figures and are for convenience of description and simplification, not indicating or implying that the device or component must have a specific orientation, construction, or operation, and should not be understood as a limitation of the present application.

Moreover, the terms "first" and "second" are used merely for descriptive purposes and should not be understood as indicating or implying relative importance or the number of the technical features. Therefore, features with "first" or "second" can explicitly or implicitly include at least one such feature. The term "multiple" in this application means at least two, such as two, three, etc., unless otherwise clearly specified.

Additionally, some of the above terms, in addition to indicating orientation or positional relationships, may also indicate other meanings. For example, the term "up" may sometimes also indicate a dependency or connecting relationship. Those skilled in the art can understand these terms in the context of the present application.

Breastfeeding provides many benefits for both infants and breastfeeding women. Breast milk contains all the nutrients required for the infant's growth and development. Breastfed infants are healthier, with fewer ear infections, respiratory infections, and a lower risk of allergies, cancer, childhood diabetes, and obesity. They are also less likely to develop heart disease, eczema, and asthma. For breastfeeding women, breastfeeding can reduce the likelihood of postpartum bleeding and anemia, help the uterus return to its pre-pregnancy size, and burn an additional 500 calories per day.

However, due to work schedules and other time constraints, not every breastfeeding woman is able to breastfeed on demand. Therefore, many breastfeeding women use a breast pump to express and store breast milk for later feeding. Abreast pump system typically includes a breast shield, which is a funnel-shaped device with a conical area that rests against the breast, with the nipple positioned in the center of the breast shield. When negative pressure is applied, the nipple is drawn into the tubular portion of the breast shield, usually the nipple channel. The nipple channel of the breast shield is connected to other components of the breast milk collection kit. This connecting allows intermittent (i.e., cyclic) negative pressure to be applied inside the breast shield, while also providing a flow path for the expressed milk to enter the nipple channel and be collected in a collection container. The collection container can be a breast milk container with a threaded cap, which can also serve as a feeding bottle for the baby. Breastfeeding women typically need to hold the breast shield in place manually in order to express milk.

It is foreseeable that securing the breast shield can be inconvenient and limits the tasks a woman can perform while expressing milk. Although various bras and tops have been developed to secure the breast shield, these bras and tops generally do not adequately secure the breast shield, requiring frequent adjustments.

In the embodiment of this application, the nursing garment can take the form of a bra, top, shirt, tank top, camisole, sleepwear, dress, or other types of women's clothing, not limited to the bra shown in the figures. Specifically, the nursing garment may be a nursing bra, nursing top, nursing shirt, nursing tank top, nursing camisole, nursing sleepwear, nursing dress, or any other women's garment designed for breastfeeding. The nursing garment may also be a breast pump bra, breast pump top, breast pump shirt, breast pump tank top, breast pump camisole, breast pump sleepwear, breast pump dress, or other women's clothing designed to support a breast pump. The nursing garment may further combine both the breast pump and breastfeeding functions. In such a case, the garment could be a breast pump/nursing bra, breast pump/nursing top, breast pump/nursing shirt, breast pump/nursing tank top, breast pump/nursing camisole, breast pump/nursing sleepwear, breast pump/nursing dress, or any other garment designed to support either the breast pump or breastfeeding. The nursing garment is configured to allow breastfeeding women to express milk or nurse their babies without needing to remove the garment.

Figure 2:
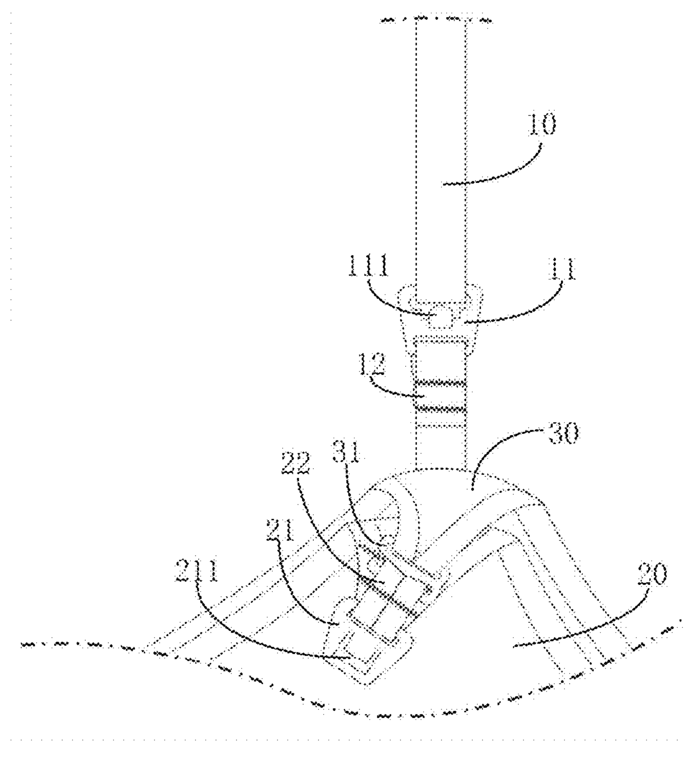
FIG. 2 is a schematic partial view of the nursing garment in one embodiment of the present application, showing the state where the inner layer and outer layer are connected, and the outer layer and shoulder strap are detached.
Figure 3:
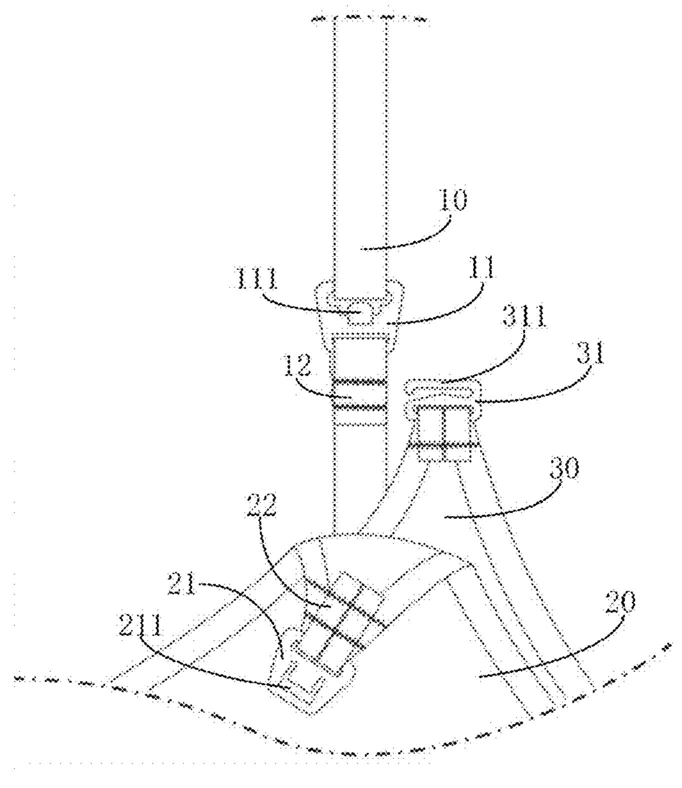
FIG. 3 is a schematic partial view of the nursing garment in one embodiment of the present application, showing the state where the inner layer and outer layer are detached, and the outer layer and shoulder strap are detached.
Figure 4:
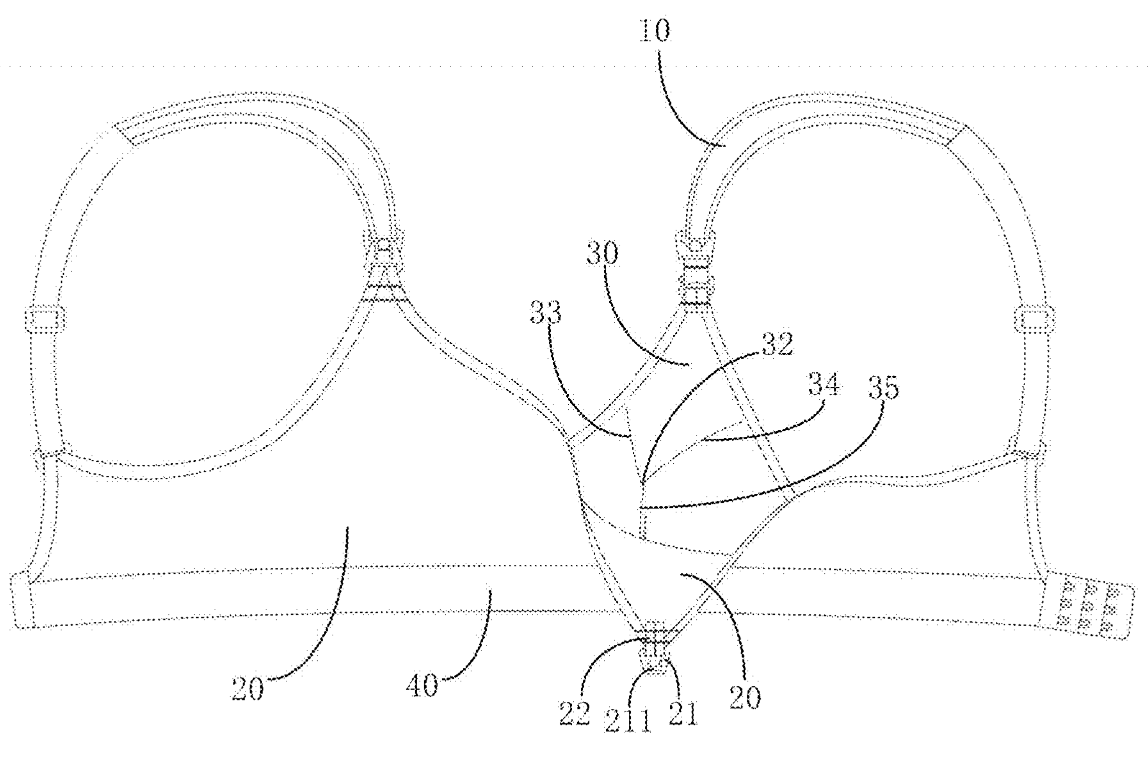
FIG. 4 is a schematic front view of the nursing garment in one embodiment of the present application, showing the state where the outer layer and shoulder strap are detached, and the inner layer and shoulder strap are connected.
Figure 5:
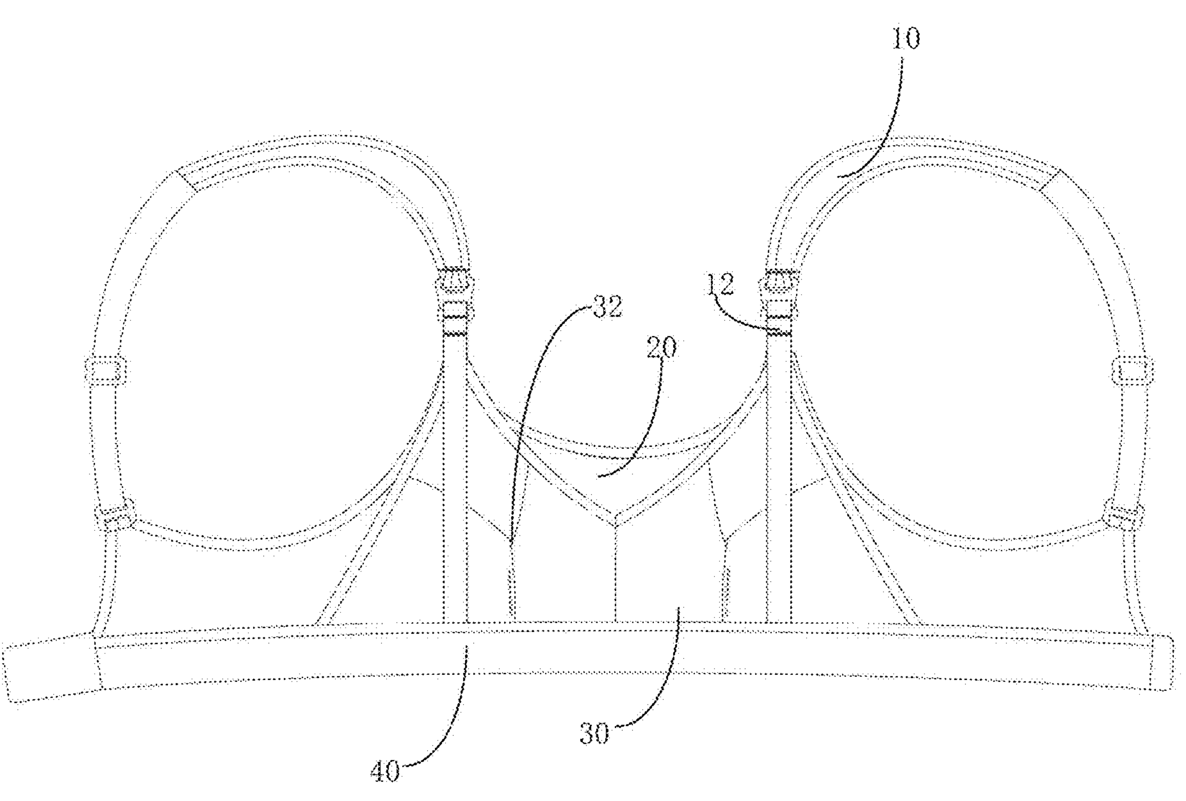
FIG. 5 is a schematic rear view of the nursing garment in one embodiment of the present application.
Figure 6:
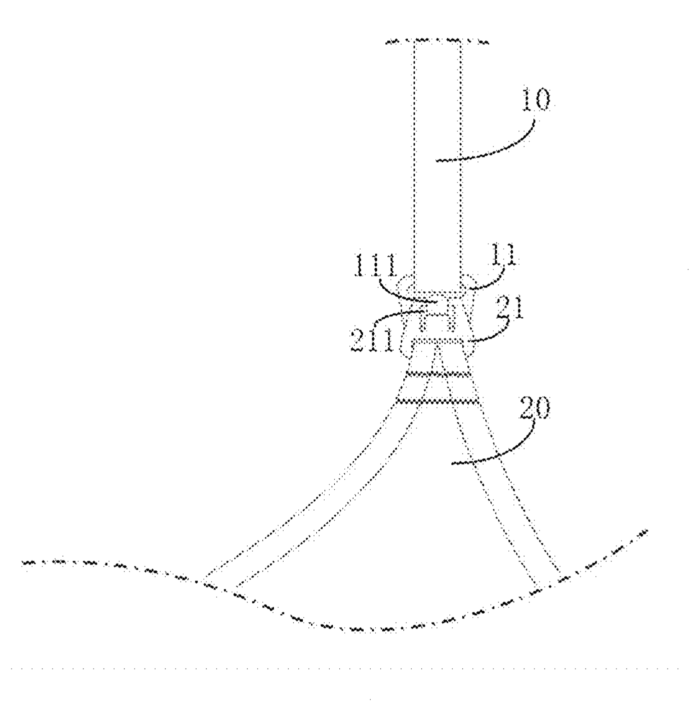
FIG. 6 is a schematic partial view of the nursing garment in one embodiment of the present application, showing the state where the inner layer and outer layer are connected, and the outer layer and shoulder strap are connected.
Figure 7:
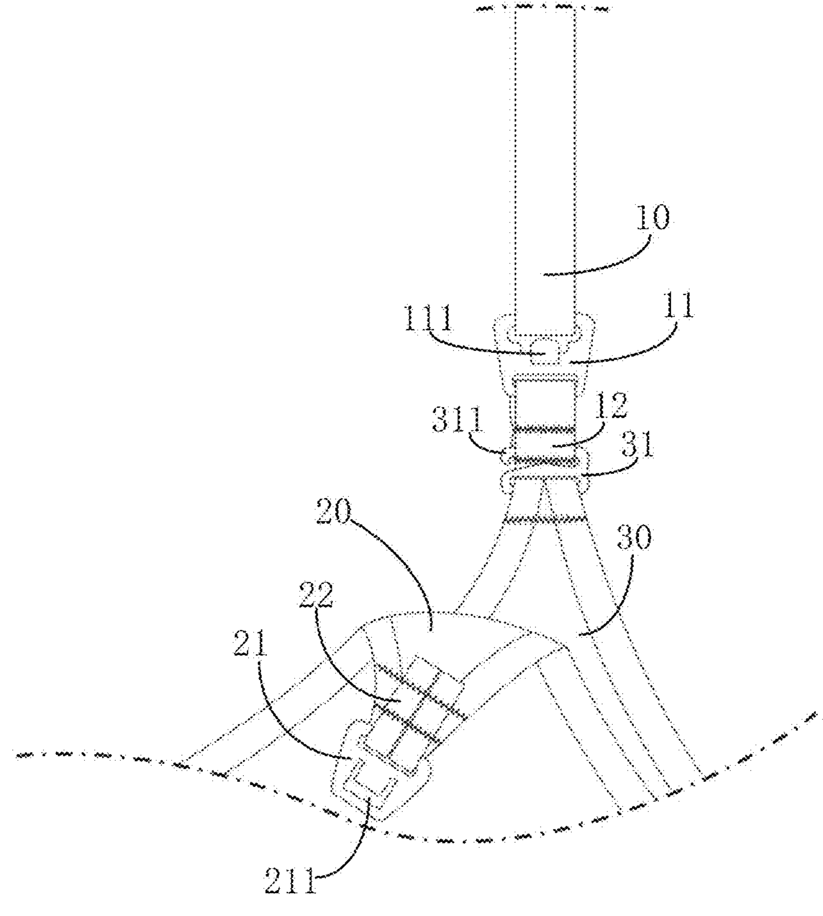
FIG. 7 is a schematic partial view of the nursing garment in one embodiment of the present application, showing the state where the outer layer and shoulder strap are detached, and the inner layer and shoulder strap are connected.

Please refer to FIGS. 1 to 7. FIG. 1 is a schematic side view of the nursing garment in one embodiment of the present application, showing the state where the inner layer and the outer layer are detached, and the outer layer and shoulder strap are detached. FIG. 2 is a schematic partial view of the nursing garment in one embodiment of the present application, showing the state where the inner layer and outer layer are connected, and the outer layer and shoulder strap are detached. FIG. 3 is a schematic partial view of the nursing garment in one embodiment of the present application, showing the state where the inner layer and outer layer are detached, and the outer layer and shoulder strap are detached. FIG. 4 is a schematic front view of the nursing garment in one embodiment of the present application, showing the state where the outer layer and shoulder strap are detached, and the inner layer and shoulder strap are connected. FIG. 5 is a schematic rear view of the nursing garment in one embodiment of the present application. FIG. 6 is a schematic partial view of the nursing garment in one embodiment of the present application, showing the state where the inner layer and outer layer are connected, and the outer layer and shoulder strap are connected. FIG. 7 is a schematic partial view of the nursing garment in one embodiment of the present application, showing the state where the outer layer and shoulder strap are detached, and the inner layer and shoulder strap are connected.

As shown in FIGS. 1, 4, and 5, the embodiment of the present application is explained using a nursing garment in the form of a bra as an example. The nursing garment may include a shoulder strap 10, an outer layer 20, and an inner layer 30. In some embodiments, the nursing garment may further include a band 40 around the chest, which is configured to wrap around the wearer's torso when worn. The lower ends of the inner layer 30 and outer layer 20 are connected to the band 40. Both the outer layer 20 and the inner layer 30 can rotate relative to the band 40. The inner layer 30 is positioned closer to the wearer than the outer layer 20 when the nursing garment is worn.

As shown in FIGS. 1, 2, and 3, the shoulder strap 10 has a first connecting structure 11. The outer layer 20 has a second connecting structure 21, the second connecting structure 21 is detachably connectable to the first connecting structure 11. The inner layer 30 has a third connecting structure 31. The outer layer 20 has a fourth connecting structure 22, and the third connecting structure 31 is detachably connectable to the fourth connecting structure 22.

As shown in FIGS. 4 and 5, the inner layer 30 has an opening 32, and the opening 32 is configured to support at least a portion of a breast pump inserted into the opening 32, or the opening 32 is configured to allow the wearer's nipple to be exposed through the opening 32 for breastfeeding. The outer layer 20 is detachably connectable to the shoulder strap 10 via the second connecting structure 21, such that the outer layer and the inner layer can be detached from the shoulder strap together, thereby at least partially exposing the wearer's breast.

In one embodiment, the opening 32 is formed between three edges 33, 34, 35 of the inner layer 30, with the three edges 33, 34, 35 at least partially overlap. The opening 32 in this embodiment is suitable for supporting a breast pump, providing stable support for the breast pump through the three edges 33, 34, 35. These three edges 33, 34, 35 are located on the inner side of the inner layer 30, not on the outer side. Any two of these three edges 33, 34, 35 are not parallel to each other.

In one embodiment, the elasticity of the three edges 33, 34, 35 is greater than the elasticity of other portions of the inner layer 30. By increasing the elasticity of these three edges 33, 34, 35 compared to other areas, they can contract to provide stable support when supporting the breast pump. In some embodiments, the three edges 33, 34, 35 can be reinforced using an adhesive process, by applying one or more layers of reinforcing strips, where the adhesive film in the middle has elasticity.

In some embodiments, the opening may also be a slit formed on the inner layer. In this embodiment, the slit allows part of the wearer's breast, such as the nipple, to pass through for breastfeeding.

It should be understood that the shape and structure of the opening are not limited to the embodiment described in the application, as long as they can support a breast pump or allow the nipple to pass through for breastfeeding.

As shown in FIG. 3, in one embodiment of the present application, the first connecting structure 11 is a first clasp 11, and the second connecting structure 21 is a second clasp 21. The first clasp 11 has a first hook 111, and the second clasp 21 has a slot 211, where the slot 211 is matched with the first hook 111 to achieve a detachable connecting between the first connecting structure 11 and second connecting structures 21. The slot 211 is generally U-shaped, forming a resilient structure on the inside of the slot 211. This allows some elastic space when the first hook 111 is engaged with the slot 211, improving the ease of connecting and detachment.

In one embodiment, the third connecting structure 31 is a second clasp 31, and the fourth connecting structure 22 is a first loop 22. The second clasp 31 has a second hook 311, which is matched with the first loop 22.

Alternatively, the first loop 22 is provided on the inner surface of the outer layer 20. In this embodiment, the first loop 22 is a sewn loop on the inner surface of the outer layer 20, formed by sewing the ends of a fabric strip to the outer layer 20. In some embodiments, the first loop can be formed using an adhesive process, meaning the two ends of a fabric strip are adhered to the inner surface of the outer layer 20 via an adhesive film to form the loop structure.

In one embodiment, one of the first and second connecting structures is a hook structure, and the other is a loop structure, slot structure, or hole structure.

In one embodiment, one of the third and fourth connecting structures is a hook structure, and the other is a loop structure, slot structure, or hole structure.

In other embodiments, one of the first and second connecting structures may be the hook side of hook-and-loop fasteners, and the other may be the loop side of hook-and-loop fasteners.

In other embodiments, one of the third and fourth connecting structures may be the hook side of hook-and-loop fasteners, and the other may be the loop side of hook-and-loop fasteners.

In other embodiments, the first and second connecting structures may adopt other detachable connecting structures, which are not limited by the present embodiment. Similarly, the third and fourth connecting structures can use other detachable connecting structures, which are not limited by the present embodiment.

As shown in FIGS. 1, 3, and 7, in one embodiment, the shoulder strap 10 has a fifth connecting structure 12, and the third connecting structure 31 of the inner layer 30 is selectively connectable to either the fourth connecting structure 22 or the fifth connecting structure 12. After the outer layer 20 and inner layer 30 are detached from the shoulder strap 10, the inner layer 30 is connectable to the fifth connecting structure 12 via the third connecting structure 31 to allow the inner layer 30 to support at least a portion of a breast pump inserted into the opening 32, or to allow the wearer's nipple to be exposed through the opening 32 for breastfeeding.

Alternatively, the fifth connecting structure 12 is a second loop 12 provided on the shoulder strap 10. This can be a sewn loop formed by sewing the ends of a fabric strip into the shoulder strap 10. In some embodiments, the second loop may be formed using an adhesive process, meaning the two ends of a fabric strip are adhered to the surface of the shoulder strap 10 via an adhesive film to form the loop structure.

In one embodiment, the inner layer 30 and outer layer 20 are made of the same fabric material. In other embodiments, the inner layer 30 and outer layer 20 may be made of different fabric materials. For example, the inner layer 30 can be made of a more skin-friendly fabric, while the outer layer 20 may be made of waterproof, wear-resistant, or other materials. This is not limited by the present embodiment.

In this embodiment, the fifth connecting structure 12 and the first connecting structure 11 are different structures located in different positions. The first connecting structure 11 is a hook, while the fifth connecting structure 12 is a loop structure. It should be understood that in other embodiments, the fifth connecting structure and the first connecting structure may be the same structure, meaning that the first connecting structure can also function as the fifth connecting structure. In other words, the third connecting structure 31 on the inner layer 30 can selectively connect to the fourth connecting structure 33 or the first connecting structure 11. After the outer layer 20 and inner layer 30 are detached from the shoulder strap 10, the inner layer 30 can connect to the first connecting structure 11 via the third connecting structure 31, allowing the inner layer 30 to support at least part of a breast pump inserted into the opening 32, or allowing the wearer's nipple to protrude through the opening 32 for breastfeeding.

The following describes the use scenarios of the nursing garment in the embodiment of the present application, in conjunction with the accompanying drawings.

As shown in FIG. 6, in one use scenario, the inner layer 30 is connected to the outer layer 20 via the third connecting structure 31 and the fourth connecting structure 22. The outer layer 20 is connected to the shoulder strap 10 via the first connecting structure 11 and the second connecting structure 21. In this scenario, the nursing garment is worn as a normal piece of clothing, ensuring the privacy of the wearer's chest.

As shown in FIG. 2, in another use scenario, the second connecting structure 21 of the outer layer 20 is detached from the first connecting structure 11 on the shoulder strap 10, and the inner layer 30 is connected to the outer layer 20 through the third connecting structure 31 and the fourth connecting structure 22. This configuration allows at least part of the wearer's breast to be exposed through the nursing garment for breastfeeding.

As shown in FIGS. 4 and 7, in another use scenario, the second connecting structure 21 of the outer layer 20 is detached from the first connecting structure 11 on the shoulder strap 10, and the inner layer 30 is connected to the fifth connecting structure 12 on the shoulder strap 10 via the third connecting structure 31. This allows the inner layer 30 to support at least part of a breast pump inserted into the opening 32 or allows the wearer's nipple to protrude through the opening 32 for breastfeeding.

The embodiment of the present application provides a nursing garment, which includes: shoulder straps, with a first connecting structure provided on the shoulder straps; an outer layer, with a second connecting structure provided on the outer layer, and the second connecting structure being detachably connected to the first connecting structure; and an inner layer, with a third connecting structure provided on the inner layer, and the outer layer being provided with a fourth connecting structure, with the third and fourth connecting structures being detachably connected. The inner layer is provided with an opening, which is configured to support at least part of a breast pump inserted into the opening or to allow the wearer's nipple to protrude through the opening for breastfeeding. The outer layer can be detachably connected to the shoulder straps via the second connecting structure, such that the outer layer and the inner layer can be detached from the shoulder strap together, thereby at least partially exposing the wearer's breast. This ensures smooth disassembly and connecting of the layers of the nursing garment.

To further clarify the objectives, technical solutions, and advantages of the present application, the following detailed description, along with the accompanying drawings and embodiments, is provided. It should be understood that the specific embodiments described here are only for explaining the present application and do not limit it.

The above is only a specific embodiment of the present application. It should be pointed out that, for those skilled in the art, various modifications and refinements can be made without departing from the principles of the present application. These modifications and refinements should also be considered within the scope of protection of the present application.

What is claimed is:

1. A nursing garment, comprising:

a shoulder strap, wherein the shoulder strap has a first connecting structure;

an outer layer, wherein the outer layer has a second connecting structure, and the second connecting structure is detachably connectable to the first connecting structure;

and an inner layer, wherein the inner layer has a third connecting structure, and the outer layer has a fourth connecting structure, and the third connecting structure is detachably connectable to the fourth connecting structure;

wherein the inner layer has an opening, and the opening is configured to support at least a portion of a breast pump inserted into the opening, or the opening is configured to allow a wearer's nipple to be exposed through the opening for breastfeeding; wherein the opening is formed between three edges of the inner layer, and the three edges at least partially overlap, both the three edges and other portions of the inner layer besides the three edges possess elasticity, and the elasticity of the three edges is greater than the elasticity of the other portions, the three edges comprise a region incorporating at least one reinforcing strip bonded to the inner layer by an elastic adhesive film;

wherein the outer layer is detachably connectable to the shoulder strap via the second connecting structure, such that the outer layer and the inner layer can be detached from the shoulder strap together, thereby when the garment is worn and when the outer layer and the inner layer are detached from the shoulder strap together, the wearer's breast is at least partially exposed.

2. The nursing garment of claim 1, wherein:

the shoulder strap has a fifth connecting structure, and the third connecting structure of the inner layer is selectively connectable to either the fourth connecting structure or the fifth connecting structure;

after the outer layer and the inner layer are detached from the shoulder strap, the inner layer is connectable to the fifth connecting structure via the third connecting structure to allow the inner layer to support at least a portion of a breast pump inserted into the opening, or the opening is configured to allow the wearer's nipple to be exposed through the opening for breastfeeding.

3. The nursing garment of claim 2, wherein the fifth connecting structure is a second loop disposed on the shoulder strap.

4. The nursing garment of claim 3, wherein the second loop is a sewn loop on the shoulder strap, and the sewn loop is formed by sewing the ends of a fabric strip to the shoulder strap.

5. The nursing garment of claim 3, wherein the second loop is formed by attaching the ends of a fabric strip to the shoulder strap.

6. The nursing garment of claim 1, wherein one of the first connecting structure and the second connecting structure is a hook structure, and the other is a loop structure, slot structure, or hole structure.

7. The nursing garment of claim 1, wherein one of the third connecting structure and the fourth connecting structure is a hook structure, and the other is a loop structure, slot structure, or hole structure.

8. The nursing garment of claim 1, wherein one of the first connecting structure and the second connecting structure is a hook side of a hook-and-loop fastener, and the other is the loop side of the hook-and-loop fastener.

9. The nursing garment of claim 1, wherein one of the third connecting structure and the fourth connecting structure is a hook side of a hook-and-loop fastener, and the other is the loop side of the hook-and-loop fastener.

10. The nursing garment of claim 1, wherein the first connecting structure is a first clasp, the second connecting structure is a second clasp, the first clasp has a first hook, and the second clasp has a slot, wherein the slot is configured to match the first hook.

11. The nursing garment of claim 1, wherein the third connecting structure is a second clasp, the fourth connecting structure is a first loop, the second clasp has a second hook, and the second hook is configured to match the first loop.

12. The nursing garment of claim 11, wherein the first loop is disposed on the inner surface of the outer layer.

13. The nursing garment of claim 11, wherein the first loop is a sewn loop on the inner surface of the outer layer, the sewn loop is formed by sewing the ends of a fabric strip to the outer layer.

14. The nursing garment of claim 11, wherein the first loop is formed by attaching the ends of a fabric strip to the outer layer.

15. The nursing garment of claim 1, wherein any two of the three edges are not parallel to each other.

16. The nursing garment of claim 1, wherein the inner layer and the outer layer are made of different fabrics.

17. The nursing garment of claim 1, wherein the opening is a slit formed on the inner layer.

18. The nursing garment of claim 1, wherein the inner layer and the outer layer are made of the same fabric.

* * * * *